(12) United States Patent
Kyota et al.

(10) Patent No.: US 7,623,751 B2
(45) Date of Patent: Nov. 24, 2009

(54) COMPOUND, POLYMERIZABLE COMPOSITION, OPTICAL DEVICE, AND METHOD FOR PRODUCING REFRACTIVE INDEX PROFILE OPTICAL DEVICE

(75) Inventors: Hirokazu Kyota, Kanagawa (JP); Hiroki Sasaki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 162 days.

(21) Appl. No.: 11/718,536

(22) PCT Filed: Nov. 4, 2005

(86) PCT No.: PCT/JP2005/020661
§ 371 (c)(1),
(2), (4) Date: May 3, 2007

(87) PCT Pub. No.: WO2006/049321
PCT Pub. Date: May 11, 2006

(65) Prior Publication Data
US 2008/0226244 A1     Sep. 18, 2008

(30) Foreign Application Priority Data
Nov. 5, 2004    (JP)    ............... 2004-322567

(51) Int. Cl.
*G02B 6/00*    (2006.01)
*C08G 59/42*    (2006.01)

(52) U.S. Cl. .................... 385/143; 385/145; 522/51

(58) Field of Classification Search ......... 385/141–145; 522/51
See application file for complete search history.

(56) References Cited

FOREIGN PATENT DOCUMENTS

| JP | 61-200144 A | | 9/1986 |
|---|---|---|---|
| JP | 62-198854 A | | 9/1987 |
| JP | 63-065092 | * | 3/1988 |
| JP | 63-065092 A | | 3/1988 |
| JP | 2003-192708 A | | 7/2003 |
| JP | 2004-224708 A | | 8/2004 |
| JP | 2004-224840 A | | 8/2004 |

OTHER PUBLICATIONS

Kovacic, P, A. Kyriakis, "Polymerization of Benzene to p-Polyphenyl by Aluminum Chloride-Cupric Chloride", J. Am. Chem. Soc., 1963, 85 (4), pp. 454-458.*

* cited by examiner

*Primary Examiner*—Charlie Peng
(74) *Attorney, Agent, or Firm*—Sughrue Mion, PLLC

(57) ABSTRACT

Using a compound of the following formula (1) makes it possible to provide an optical device having a reduced transmission loss.

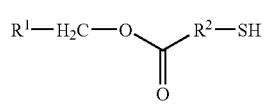

Formula (1)

wherein $R^1$ is an alkyl group having from 1 to 3 carbon atoms and having at least one fluorine atom, and $R^2$ is an alkylene group having 1 or 2 carbon atoms.

17 Claims, No Drawings

COMPOUND, POLYMERIZABLE COMPOSITION, OPTICAL DEVICE, AND METHOD FOR PRODUCING REFRACTIVE INDEX PROFILE OPTICAL DEVICE

TECHNICAL FIELD

The present invention belongs to a technical field of a compound, a polymerizable composition for forming an optical device, an optical device formed of the composition, and a method for producing the optical device.

BACKGROUND ART

Plastic optical devices are generally superior to glass-based optical devices having the same constitution in that they are easy to produce and work and they are inexpensive. Recently, therefore, their applications have been tried to various fields of optical fibers, optical lenses and optical waveguides. Of such optical devices, plastic optical fibers (hereinafter referred to as POFs) are flexible, though having a disadvantage in that their transmission loss is relatively larger than that of glass-based optical fibers since their nude wires are entirely formed of plastics. In addition, they are lightweight and have good workability, and, as compared with glass-based optical fibers, they may be readily produced as large-diameter fibers. Still another advantage of POFs is that they may be produced at low costs. Accordingly, various investigations have been made for their applicability to short-distance optical communication transmission media not involving a problem of transmission loss.

In general, a plastic optical fiber comprises a core of an organic compound with a polymer as its matrix, and a clad (outer shell) of an organic compound having a different refractive index from that of the core (generally having a low refractive index). Recently in particular, a refractive index profile, plastic optical fiber, in which the core has a refractive index profile that varies from its center to its outside, has become specifically noticed as an optical fiber having a high transmission capacity, since it accepts a broad optical signal zone for transmission through it. One method proposed for producing the optical fiber of the type comprises preparing an optical fiber preform by the use of a refractive index-controlling agent, and then stretching the preform.

In preparing the preform, in general, a monomer for it is polymerized with a thiol such as n-dodecanethiol serving as a chain transfer agent added thereto. This is because if the polymerization is carried out in the absence of a chain transfer agent, then the molecular weight of the polymer produced may be too large and may be therefore difficult to stretch. However, it is known that some chain transfer agent may remain in the polymer produced and may increase the transmission loss through the polymer. In particular, this is remarkable when a fluorine-containing monomer is polymerized to give a polymer material for optical devices. To solve the problem, using a perfluoroalkyl group-containing thiol as a chain transfer agent is under investigation (JP-A 2003-192708). However, the chain transfer agent in this reference is limited in point of the type of monomer that may be combined with it, and its latitude in general use thereof is narrow.

On the other hand, for solving the problem of an odor of a thiol-based chain transfer agent, it is known that an ester structure-containing thiol may be effective in polymerization of a styrene-acrylic monomer (JP-A 2004-224708, 2004-224840). However, no one knows an example of using it for optical devices.

DISCLOSURE OF THE INVENTION

A subject matter of the invention is to provide a chain transfer agent which may be used in production of polymethacrylates and polyacrylates useful as a material of optical devices, especially plastic optical fibers, and which is effective for reducing the transmission loss through the polymers.

We, the present inventors have assiduously studied and, as a result, have found that the above problems may be solved by the invention mentioned below:

(1) A compound of the following formula (1):

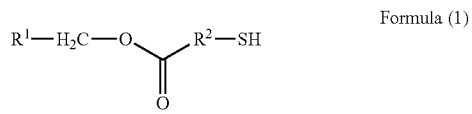

Formula (1)

wherein $R^1$ represents an alkyl group having from 1 to 3 carbon atoms and having at least one fluorine atom; and $R^2$ represents an alkylene group having 1 or 2 carbon atoms.

(2) A polymerizable composition comprising a polymerizable monomer and a compound of the formula (1).

(3) A polymerizable composition comprising a polymerizable monomer and a compound of the following formula (2), which is for forming an optical member:

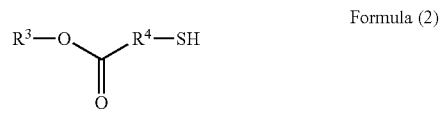

Formula (2)

wherein $R^3$ represents an alkyl group or an aryl group; and $R^4$ represents an alkylene group having from 1 to 4 carbon atoms.

(4) The polymerizable composition of (2) or (3), wherein the polymerizable monomer is an acrylate and/or a methacrylate.

(5) The polymerizable composition of any of (2) to (4), wherein a part or all of the hydrogen atoms which the polymerizable monomer has are deuterium atoms.

(6) An optical device comprising a compound produced by polymerizing the polymerizable composition of any of (2) to (5) and having a refractive index profile region where the refractive index of the compound varies.

(7) The optical device of (6), which is for optical communication using a light source at 900 nm or shorter.

(8) The optical device of (6), which is for optical communication using a light source at 700 nm or shorter.

(9) A method for producing an optical device having a core and a clad, which comprises polymerizing the polymerizable composition of any of (2) to (5) to form a core or a clad.

(10) A method for producing a refractive index profile optical device, which comprises polymerizing the polymerizable composition of any of (2) to (5) in a cylindrical chamber to thereby form a core having a gradually increasing refractive index profile.

(11) A method for producing a refractive index profile optical device, which comprises injecting a polymerizable composition for a clad into a cylindrical chamber rotating around the center axis thereof held horizontally and polymerizing it therein to form the clad, and then polymerizing a polymerizable composition for a core to form the core that has a refractive index profile gradually varying from the interface between it and the clad to the center thereof, and in which at least one of the polymerizable composition for the clad and the polymerizable composition for the core is the polymerizable composition of any of (2) to (5).

(12) A method for producing a refractive index profile optical device, which comprises injecting the polymerizable composition of any of (2) to (5) into a cylindrical chamber rotating around the center axis thereof held horizontally and polymerizing it therein to form a clad, and then polymerizing the polymerizable composition of any of (2) to (5) to form a core that has a refractive index profile gradually varying from the interface between it and the clad to the center thereof.

(13) An optical device comprising a compound of the formula (1).

BEST MODE FOR CARRYING OUT THE INVENTION

The invention is described in detail hereinunder. In this description, the numerical range expressed by the wording "a number to another number" means the range that falls between the former number indicating the lowermost limit of the range and the latter number indicating the uppermost limit thereof.

The compound of formula (1) of the invention is described.

The compound of formula (1) is a compound group favorable for the chain transfer agent for use in the invention. There is known no report indicating the synthetic production of the compound. We the present inventors have newly produced the compound.

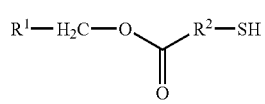

Formula (1)

In formula (1), $R^1$ represents an alkyl group having from 1 to 3 carbon atoms and having at least one fluorine atom. Preferably, at least 50% of the hydrogen atoms that the alkyl group has are substituted with fluorine atoms. Concrete examples of the group are a 2,2,2-trifluoroethyl group, a 2,2,3,3-tetrafluoropropyl group, and a 2,2,3,3,3-pentafluoropropyl group.

$R^2$ represents an alkylene group having 1 or 2 carbon atoms, such as —$CH_2$—, —$CH_2CH_2$— or —$CH(CH_3)$—.

The hydrogen atom in the compound of formula (1) may be either a light hydrogen atom $^1H$ or a heavy hydrogen atom (deuterium) $^2H$.

Specific examples of the thiols of formula (1) are mentioned below. In the structural formulae, the hydrogen atom may be either a light hydrogen atom $^1H$ or a heavy hydrogen atom (deuterium) $^2H$. The invention should not be limited to these compounds.

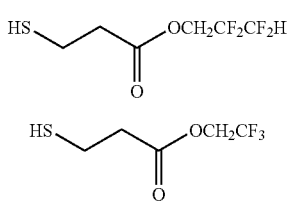

1-1

1-2

-continued

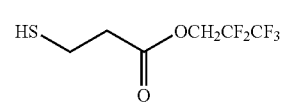

1-3

1-4

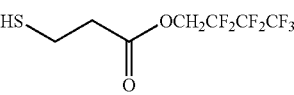

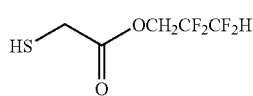

1-5

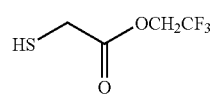

1-6

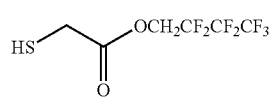

1-7

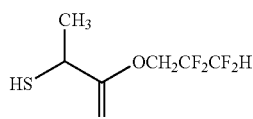

1-8

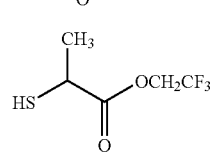

1-9

The compound of formula (2) of the invention is described.

The compound of formula (2) is used as a chain transfer agent in the invention, and it has both a mercapto group and an ester group. The compound of formula (1) mentioned above is within the scope of the compound of formula (2).

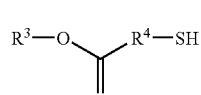

Formula (2)

In formula (2), $R^3$ represents an alkyl group or an aryl group, and is preferably an alkyl group.

The alkyl group preferably has from 1 to 12 carbon atoms, more preferably from 1 to 8 carbon atoms, and it may be linear, branched or cyclic. Concretely, it includes a methyl group, an ethyl group, a (normal or iso)-propyl group, and a cyclohexyl group. More preferably, the group has at least one fluorine atom, and even more preferably, at least 50% of the hydrogen atoms that the alkyl group has are substituted with fluorine atoms. Concrete examples of the group are a 2,2,2-trifluoroethyl group, a 2,2,3,3-tetrafluoropropyl group, and a 2,2,3,3,3-pentafluoropropyl group.

The aryl group preferably has from 6 to 18 carbon atoms, more preferably from 6 to 12 carbon atoms. Its concrete examples are a phenyl group, a tolyl group, a p-chlorophenyl group, and a pentafluorophenyl group.

$R^4$ represents an alkylene group having from 1 to 4 carbon atoms. Its concrete examples are —$CH_2$—, —$CH_2CH_2$—, —$CH(CH_3)$—, —$C(CH_3)_2$—, —$(CH_2)_3$—, —$(CH_2)_4$—, and a cyclopropyl group. Preferred are —$CH_2$—, —$CH_2CH_2$—. Not overstepping the sprit and the scope of the invention, the hydrogen atoms constituting $R^4$ may be substituted with any other substituent.

The hydrogen atoms in formula (2) may be either a light hydrogen atom $^1H$ or a heavy hydrogen atom (deuterium) $^2H$.

Specific examples of the compounds of formula (2) for use in the invention are mentioned below. In the structural formulae, the hydrogen atom may be either a light hydrogen atom $^1H$ or a heavy hydrogen atom (deuterium) $^2H$. The invention should not be limited to these compounds.

For producing the compounds of formula (1) and/or formula (2), herein employable is any known method of thermal condensation of the corresponding, mercapto group-containing carboxylic acid and an alcohol in the presence of an acid. For example, employable is the method described in a reference, *Bull. Soc. Chim. Beig.;* 1988, 97, 535 (in which an acid, p-toluenesulfonic acid is used).

Concrete examples of the production are described in detail in the section of Examples.

The polymerizable composition of the invention is described.

The polymerizable composition of the invention comprises a polymerizable monomer and a chain transfer agent. For application to optical devices, it may comprise a polymerization initiator to initiate the polymerization of the polymerizable monomer therein. The polymerizable composition of the invention may be used for producing optical devices, especially refractive index profile optical devices having a refractive index profile. The materials are described in detail hereinunder.

(Polymerizable Monomer)

Though not specifically defined in point of its type, the polymerizable monomer for use in the invention preferably comprises, as the principal ingredient thereof, an acrylate and/or a methacrylate (hereinafter referred to as "(meth)acrylate"). The wording "comprises, as the principal ingredient thereof", as referred to herein, means that the composition may include a copolymer of a (meth)acrylate and any other monomer (e.g., styrene, maleimide), not detracting from the optical properties of the composition. Preferably, however, the composition comprises a (meth)acrylate in an amount of at least 50% by mass of all the monomers therein, more preferably in an amount of at least 70% by mass, most preferably in an amount of 100% by mass (that is, the monomer in the composition is entirely a (meth)acrylate).

Preferably, at least a part of the hydrogen atoms constituting the (meth) acrylate are substituted with deuterium atoms, since the light transmission loss through the polymer owing to the C—H stretching vibration therein could be reduced. In this case, it is desirable that at least 70% of all the hydrogen atoms constituting the (meth) acrylate are substituted with deuterium atoms. When a (meth)acrylate substituted with a halogen atom, especially preferably a fluorine atom is used, then it is desirable since it may readily produce a refractive index difference between its polymer and a copolymer with a halogen-free monomer, and, as a result, a refractive index profile device may be readily formed. In this case, it is desirable that at least 15% of all the hydrogen atoms constituting the (meth) acrylate are substituted with a halogen atom. Specific examples of the (meth)acrylates usable in the invention are mentioned below, to which, however, the invention should not be limited.

(a) Fluorine-free methacrylates and fluorine-free acrylates:

Methyl methacrylate, ethyl methacrylate, isopropyl methacrylate, b-butyl methacrylate, benzyl methacrylate, phenyl methacrylate, cyclohexyl methacrylate, diphenylmethyl methacrylate, tricyclo[$5.2.1.0^{2.6}$]decanyl methacrylate, adamantyl methacrylate, isobornyl methacrylate; methyl acrylate, ethyl acrylate, t-butyl acrylate, phenyl acrylate.

(b) Fluorine-containing acrylate and fluorine-containing methacrylates:

2,2,2-trifluoroethyl methacrylate, 2,2,3,3-tetrafluoropropyl methacrylate, 2,2,3,3,3-pentafluoropropyl methacrylate, 1-trifluoromethyl-2,2,2-trifluoroethyl methacrylate, 2,2,3,3,4,4,5,5-octafluoropentyl methacrylate, 2,2,3,3,4,4-hexafluorobutyl methacrylate.

In the invention, any other polymerizable monomers than the above-mentioned (meth)acrylates are employable. Specific examples of the other polymerizable monomers usable in the invention are mentioned below, to which, however, the invention should not be limited.

(c) Styrenic compounds:

Styrene, α-methylstyrene, chlorostyrene, bromostyrene.

(d) Vinyl esters:

Vinyl acetate, vinyl benzoate, vinylphenyl acetate, vinyl chloroacetate.

(Polymerization Initiator)

When the polymerizable composition of the invention comprises a polymerization initiator, then the polymerization initiator therein may be suitably selected depending on the type of the monomer therein and on the polymerization mode for it. For example, preferred examples of the polymerization initiator for use herein are peroxide compounds such as benzoyl peroxide (BPO), tert-butylperoxy-2-ethylhexanoate (PBO), di-tert-butyl peroxide (PBD), tert-butylperoxyisopropyl carbonate (PBI), n-butyl-4,4-bis(tert-butylperoxy)valerate (PHV); and azo compounds such as 2,2'-azobisisobutyronitrile, 2,2'-azobis(2-methylbutyronitrile), 1,1'-azobis(cyclohexane-1-carbonitrile), as in WO93/08488.

Two or more different types of polymerization initiators may be used, as combined.

The amount of the polymerization initiator to be in the polymerizable composition may be suitably determined, depending on the type of the polymerizable monomer therein. For example, when a (meth)acrylate is used as the polymerizable monomer, then the amount of the polymerization initiator to be in the composition is preferably from 0.01 to 1% by weight of all the monomers therein.

(Chain Transfer Agent)

The invention includes a compound of formula (2) (a compound of formula (1)) as a chain transfer agent. The chain transfer agent is used essentially for controlling the molecular weight of the polymer produced. The type and the amount of the chain transfer agent for use herein may be suitably selected and determined depending on the type of the polymerizable monomer used herein. For example, when a (meth)acrylate is used as the polymerizable monomer, then it is desirable that a compound of formula (2) (a compound of formula (1)) is used in an amount of from 0.01 to 1% by weight of all the monomers. In the invention, an ester structure-containing thiol is used as the chain transfer agent, and it reduces the transmission loss through the polymer produced and improves the light transmittability of the polymer. Two or more different types of chain transfer agents may be used herein, as combined. In this case, at least one chain transfer agent shall be a compound of formula (2) (a compound of formula (1)) of the invention.

(Dopant)

The polymerizable composition of the invention may comprise a compound having a refractive index different from that of the polymerizable monomer therein (this may be hereinafter referred to as "dopant"). When the polymerizable composition of the invention comprises such a dopant and when it has a dopant concentration profile, then it may give a refractive index profile optical device. The dopant is characterized in that the solubility parameter difference between the dopant and the polymer produced through polymerization of the monomer is within 7 $(cal/cm^3)^{1/2}$, that the refractive index of the composition comprising the dopant differs from that of the composition not comprising it (preferably the former is higher than the latter) and that the refractive index difference between the two is at least 0.001, as in WO93/08488 and JP-A 5-173026. Having the property, a material which is stable under the polymerization condition (e.g., heating, irradiation with light, pressure application) of the polymerizable monomer, which can coexist in the composition along with the polymer produced, and which does not copolymerize with the monomer that is to constitute the polymer can be used as the dopant. For example, preferred are benzyl benzoate (BEN), diphenyl sulfide (DPS), triphenyl phosphite (TPP), benzyl-n-butyl phthalate (BBP), diphenyl phthalate (DPP), biphenyl (DP), diphenylmethane (DPM), tricresyl phosphate (TCP), diphenyl sulfoxide (DPSO); more preferred are BEN, DPS, TPP, DPSO. In addition to these low-molecular organic compounds, the dopant may include di- to deca-oligomers. Two or more different types of such low-molecular organic compounds for refractivity control may be combined for use herein.

The type and the amount of the dopant to be in the polymerizable composition may be suitably selected and determined depending on the type of the polymerizable monomer therein. For example, when a (meth)acrylate is used as the polymerizable monomer, then the amount of the dopant is preferably from 0.1 to 30% by weight of all the monomers in the composition.

The optical device produced by the use of the polymerizable composition of the invention is described. The optical device comprises, for example, a core and a clad around it. Preferably, the optical device of the invention has a "refractive index profile region" where the refractive index thereof smoothly increases from the outside of the core toward the center thereof. For making the optical device have such a refractive index profile region, preferably employed herein are a method of polymerizing a monomer along with a non-polymerizable refractivity-increasing agent having a higher refractive index than the monomer (dopant), as in WO93/08488 and JP-A 8-262240; and a method of polymerizing plural monomers having a different refractive index with gradually varying their blend ratio, as in JP-A 2001-215345. For example, a preform comprising an inner clad, an outer clad and a core is described for the optical device of the type. Regarding the refractive index profile in the cross-sectional direction thereof, the preform is preferably so designed that the refractive index profile coefficient of the core that is to be the essential light-guide part of the device is from 1.5 to 4.

The materials for the clad and the core in the invention are preferably those having an extremely high light transmittability. Also preferably, they are polymers not having optical anisotropy. Also preferably, the polymer for the core material and the polymer for the clad material may well adhere to each other, more preferably, the two polymers both have good mechanical properties such as good toughness and have good wet heat resistance.

Concretely, the material of the core in the invention is preferably the above-mentioned polymerizable composition.

Concretely, the material for the clad in the invention is preferably an organic material. In order to ensure the refractivity difference between the core and the clad, a fluorine-containing polymer is preferred for the clad. For example, preferred are polyvinylidene fluoride (PVDF); fluoro(meth) acrylate resin; fluoropolymer having a cyclic structure in its backbone chain (e.g., those formed through cyclization polymerization as in Japanese Patent No. 2,724,709); radical copolymer of a fluoroaliphatic cyclic structure-containing monomer (e.g., perfluoro(2,2-dimethyl-1,3-dioxol)) with a radical compound (e.g., tetrafluoroethylene, chlorotrifluoroethylene, perfluoro(vinyl ether)). A part of the hydrogen atoms constituting the compound may be substituted with deuterium atoms. The above-mentioned polymerizable composition is also preferably used for the clad material. In this case, it is more desirable that the polymerizable composition is also used for the core.

In the invention, the polymerization reaction may be promoted through thermal treatment under a predetermined condition, and after the polymerization, the polymer may be cooled at a predetermined cooling rate.

In that manner, a preform for a columnar light transmitter may be produced, in which the core and the clad are both plastics and the clad has a two-layered structure of an outer clad and an inner clad. Then, the preform is stretched. The preform may have a hollow in the center of the circular cross section thereof, but the hollow may disappear after the preform has been stretched, and, as a result, POF having a low transmission loss may be produced.

For stretching the preform, employable are various stretching methods as in JP-A 07-234322. Thus stretched, the preform gives POF having a desired diameter of, for example, from 200 μm to 1000 μm.

The plastic optical devices such as typically plastic optical fibers thus obtained in the manner as above have good properties in a light source region of a wavelength zone of from 650 nm to 850 nm that is popular in practical applications of plastic optical waveguides in the field of optical communication, and therefore they are favorably used in that light source wavelength zone.

In general use thereof, POF is covered with at least one protective layer for the purpose of improving the bending resistance, the weather resistance, the wet deterioration resistance, the tensile strength, the stamping resistance, the flame retardancy, the chemical resistance, the noise resistance to external light and the discoloration resistance to thereby improve the commercial value thereof.

As described hereinabove, the preform obtained in the invention is stretched to give POF, and POF is then worked in a first coating step to give an optical fiber core wire. One or more core wires are, either singly or as combined, further worked in a second coating step to give an optical cable. When the optical cable is a single fiber cable, then it may not be worked in the second coating step, but the single fiber coated with an outer coating layer in the first coating step may be directly used as an optical cable. There are known two modes of covering the optical cable. One core wire is airtightly covered with a coating material, or the outer surface of a bundle of two or more core wires as combined is airtightly covered with it. This is a contact coating mode. Alternatively, one optical fiber core or a bundle of optical fiber cores are loosely covered with a coating material with a space existing in the interface between them. This is a loose coating mode. In the loose coating mode, when the coating layer is peeled off at the joint part at which the cable is connected with a connector, then water may penetrate into the cable through its cut end and may diffuse in the lengthwise direction of the cable. Therefore, in general, the contact coating mode is preferred.

In the loose coating mode, however, the coating material is not airtightly contacted with the optical fiber core, and therefore, the advantage of this mode is that the coating layer may absorb and relieve much damage such as stress and heat applied to the optical cable. Accordingly, the loose coating mode is preferred in some applications. Regarding the water diffusion through the connector joint part in the loose coating mode, the space in the interface between the optical fiber core and the coating material may be filled with a fluid gel-like semi-solid or granular material, and the water penetration into the joint space may be thereby prevented. Further, when any other function such as heat resistance and mechanical function improvement is imparted to the semi-solid or granular material, then the optical fiber cable thus produced may have a multi-functional coating layer. The loose coating may be attained by controlling the extrusion nipple position at the crosshead die and controlling the degree of pressure reduction by the degassing device used, whereby the layer having the above-mentioned space may be formed around the core cable. The thickness of the space layer may be controlled by controlling the nipple thickness and the degree of pressure application/pressure reduction in the coating layer extrusion.

The coating layer to be formed in the first and second coating steps may comprise a flame retardant, an UV absorbent and an antioxidant added thereto not having any negative influence on the light transmittability of the coated cable.

The flame retardant may be any of halogen-containing, for example, bromine-containing resins or additives, and phosphorus-containing compounds. However, from the viewpoint of the safety for reducing toxic gas in firing, the mainstream of the flame retardant is being a metal hydroxide such as aluminium hydroxide or magnesium hydroxide. The metal hydroxide contains water as its internal crystal water therein. The water results from the water adhesion to the metal hydroxide during its production process, and completely removing it may be impossible. Accordingly, the flame retardation by the use of such a metal hydroxide is preferably attained by adding it to the outermost coating layer of the cable but not adding it to the coating layer that is in direct contact with POF.

For imparting any other different functions to the optical cable, any additional functional coating layers may be suitably laminated at any desired position. For example, in addition to the above-mentioned flame-retardant layer, a barrier layer for inhibiting moisture absorption of POF and a moisture-absorbing material layer for removing moisture from POF may be formed. For forming such a moisture-absorbing material layer, for example, a moisture-absorbing tape or a moisture-absorbing gel may be formed inside a predetermined coating layer or between coating layers. The other functional layers are, for example, a flexible material layer for stress relaxation when the cable is bent, a foam material layer serving as a buffer for external stress relaxation, and a reinforcing layer for increasing the toughness of the cable. Except resin, any other structural material may be used for constituting the optical cable. For example, thermoplastic resin that comprises high-elasticity fibers (high-strength fibers) and/or wires such as high-rigidity metal wires are preferably used for reinforcing the mechanical strength of the optical cable.

The high-strength fibers are, for example, aramid fibers, polyester fibers, polyamide fibers. The metal wires are, for example, stainless wires, zinc alloy wires, copper wires. However, these are not limitative. In addition, an outer metal tube sheathing for cable protection, a supporting wire for overhead cable construction, and any other function for improving wiring operation may be inserted into the outer periphery of the optical cable.

The optical cable may have any desired shape, depending on its use. For example, a bundle cable formed by concentrically bundling optical fiber cores, a tape cable formed by aligning them in lines, a covered cable formed by covering them with a presser coat or a wrapping sheath may be employed depending on the use of the optical cable.

As compared with an ordinary optical cable, the optical cable obtained from the preform of the invention has a broader latitude in axis shifting, and therefore, it may be butt-jointed. Preferably, however, an optical connector for joint is disposed at the end of the optical cable, and the cables are surely fixed and connected via the optical connector therebetween. The connector may be any known, commercially-available one, such as PN connectors, SMA connectors, SMI connectors.

The optical cable obtained from the preform of the invention is used, favorably as combined with an optical signal processor that comprises various optical members such as light emitter, light receiver, light switch, optical isolator, optical integrated circuit, optical transmit-receive module. In this case, the optical fiber of the invention may be combined with any other optical fibers, and any known techniques relating to it may be employed. For example, reference may be made to *Base and Practice of Plastic Optical Fibers* (issued by NTS); and *Nikkei Electronics Mar.* 12, 2001, pp. 110-127 "Optical device Mounted on Printed-Wiring Board, Now or Never". Combined with various techniques disclosed in these references, the invention may be favorably applied to light-transmission systems suitable to short-range appliances for high-speed large-capacity data communication and control with no influence of electromagnetic waves thereon, typically for example, in-unit wiring for computers and various digital instruments, in-unit wiring for vehicles and ships, optical linking for optical terminals to digital devices or digital devices to each other, and indoor or in-area optical LAN for houses, apartments, factories, offices, hospitals, schools.

Further, as combined with any of those described in *IEICE TRANS. ELECTRON.*, Vol. E84-C, No. 3, March 2001, pp. 339-344, "High-Uniformity Star Coupler Using Diffused Light Transmission", and *Journal of Electronics Packaging Society*, Vol. 3, No. 6, 2000, pp. 476-480 "Interconnection by Optical Sheet Bus Technique"; disposition of light-emitting device relative to optical waveguide face, as described in JP-A 2003-152284; optical busses described in JP-A 10-123350, 2002-90571, 2001-290055; optical branching/coupling devices described in JP-A 2001-74971, 2000-329962, 2001-74966, 2001-74968, 2001-318263, 2001-311840; optical star couplers described in JP-A 2000-241655; optical signal transmission devices and optical data bus systems described in JP-A 2002-62457, 2002-101044, 2001-305395; optical signal processor described in JP-A 2002-23011; optical signal cross-connection systems described in JP-A 2001-86537; light transmission systems described in JP-A 2002-26815; multi-function systems described in JP-A 2001-339554, 2001-339555; and also other various optical waveguides, optical branching filters, optical connectors, optical couplers, optical distributors, the invention may construct higher-level optical transmission systems for multi-transmit-receive communication. Apart from the above-mentioned light-transmission applications, the invention is also applicable to any other fields of lighting (light conduction), energy transmission, illumination, and sensors.

The invention is described in more detail with reference to the following Examples, in which the material and the reagent used, their ratio, and the operation with them may be suitably modified or changed not overstepping the sprit and the scope of the invention. Accordingly, the invention should not be limitatively interpreted by the Examples mentioned below.

PRODUCTION EXAMPLE 1

Production of Compound (1-1), 2,2,3,3-tetrafluoropropyl 3-mercaptopropionate 10.0 g (0.053 mol) of p-toluenesulfonic acid monohydrate was added to a solution of 15.7 g (0.148 mol) of 3-mercaptopropionic acid in 40 ml (3 eq) of 2,2,3,3-tetrafluoropropanol, and stirred at 90° C. for 4 hours. After cooled to room temperature, 2,2,3,3-tetrafluoropropanol was evaporated away under reduced pressure (about 100 mmHg), 50 ml of water was added to it, and this was then extracted with 50 ml of diisopropyl ether. The organic layer was washed with water and saturated saline, and dried with anhydrous sodium sulfate, and the solvent was evaporated away under reduced pressure (about 100 mmHg). Through reduced pressure distillation (65-68° C./4 mmHg), it gave 14.2 g (44%) of a colorless transparent liquid (Compound 1-1).

Its $^1$H—NMR (300 MHz, CDCl$_3$) data are shown below. δ 1.66 (t, 1H, J=6.3), 2.7-2.9 (m, 4H), 4.52 (t, 2H, J=9.9), 5.88 (tt, 1H, J=40, 2.7)

EXAMPLE 1

Fabrication Example 1 of Plastic Optical Fiber, Using Compound (1-1) as Chain Transfer Agent A hollow tube of polyvinylidene fluoride resin (refractive index: 1.38) formed in a mode of melt extrusion molding and having a thickness of 1 mm, an inner diameter of 22 mm and a length of 30 cm (its one end was sealed up with the same resin) was inserted into a stainless pipe, and set in a rotary polymerization device. A monomer mixture (methyl methacrylate/isobornyl methacrylate, 8/2 by weight), from which water, polymerization inhibitor and dust had been fully removed, 0.24% (by weight of the monomer mixture) of a polymerization initiator, dimethyl 2,2'-azobisisobutyrate, and 0.3% (by weight of the monomer mixture) of a chain transfer agent, Compound (1-1) were injected into the tube, then purged with nitrogen and airtightly sealed up. While rotated at 1500 rpm, this was subjected to polymerization at 65° C. for 3 hours, then at 70° C. for 2 hours and at 90° C. for 12 hours to thereby form an inner clad (corresponding to the outermost layer of the device to be fabricated herein) having a thickness of 3 mm.

A core was formed through polymerization as follows: The hollow tube thus having the inner clad formed therein was vertically set in a pressure polymerization chamber heated at 80° C. (if desired, this was put into a glass tube and inserted into an autoclave). Next, the monomer mixture (methyl methacrylate/isobornyl methacrylate, 8/2 by weight), and a dopant, diphenyl sulfide (DPS) in an amount of 5% by weight of the monomer mixture were added to it, and 0.3% (by weight of the monomer mixture) of a polymerization initiator, di-tert-butyl peroxide and 0.6% (by weight of the monomer mixture) of a chain transfer agent, Compound (1-1) were added to it. The system was well degassed, and the polymerizable composition heated at 80° C. was gently introduced into the hollow area of the hollow tube. Then, the pressure polymerization chamber was purged with nitrogen, and then pressurized up to 0.2 MPa, in which the monomers were thermally polymerized at 100° C. for 48 hours. Next, while still kept under pressure, this was further subjected to thermal polymerization and heat treatment at 140° C. for 24 hours to give a preform. Regarding the refractive index of the optical fiber preform in its cross-sectional direction, the outer clad had a constant refractive index of 1.380, the inner clad had a constant refractive index of 1.401, and the core had a varying refractive index of from 1.401 to 1.424 (center). The refractive index distribution profile of the core shows a parabolic convex curve.

Thus obtained, the preform was melt-stretched. This was vertically downwardly inserted into a heating furnace conditioned at 220 to 260° C. Based on the intended fiber diameter (750 µm), the stretching speed was so controlled that the resulting fiber could have the intended fiber diameter as measured with a fiber size meter. Thus obtained, the fiber had a diameter of 750±9 µm. The fiber was coated with a primary coat of low-density polyethylene, and then with a secondary coat of a mixture of magnesium hydroxide with nitrile butadiene rubber and polyethylene.

The coated fiber was analyzed for its transmission loss at a light source wavelength of 650 nm, which was 130 dB/km.

COMPARATIVE EXAMPLE 1

Fabrication Example 1 of Plastic Optical Fiber, Using n-dodecanethiol as Chain Transfer Agent A coated fiber was fabricated in the same manner as that of Example 1, for which, however, the same weight of n-dodecanethiol was used as the chain transfer agent in place of Compound (1-1). The coated fiber was analyzed for its transmission loss at a light source wavelength of 650 nm, which was 180 dB/km.

EXAMPLE 2

Fabrication Example 2 of Plastic Optical Fiber, Using Compound (1-1) as Chain Transfer Agent A hollow tube of polyvinylidene fluoroethylene (PVDF) formed in a mode of melt extrusion molding and having an inner diameter of 19 mm and a length of 60 cm was prepared as an outer clad. An inner clad material was injected into the hollow area of the tube. The inner clad material was prepared as follows: 114 g of MMA-d8 (all hydrogen atoms of methyl methacrylate were deuterium atoms $^2$H) of which the water content had been reduced to at most 100 ppm through distillation was mixed with a polymerization initiator, 2,2'-azobis (2,4-dimethylvaleronitrile) (Wako Jun-yaku's V-65, having a half-value time at 70° C. of 1 hour—this is hereinafter referred to as V-65) and a chain transfer agent, Compound (1-1). The resulting mixture for the inner clad material was controlled at a predetermined temperature, and then injected into the tube. V-65 used herein was processed so as to have a water content of at most 200 ppm. The amount of V-65 and that of Compound (1-1) added to MMA-d8 were 0.04 mol % and 0.2 mol %, respectively, of the monomer. The outer clad with the inner clad material thus introduced into its hollow was set in the polymerization chamber of a rotary polymerization device in such a manner that its lengthwise direction could be horizontal. While rotated therein at 2300 rpm, this was thermally polymerized at 70° C. for 2 hours. Accordingly, a layer of PMMA-d8 was formed on the inner face of the outer clad, and this is an inner clad.

A core material was injected into the hollow area of the inner clad, at room temperature under atmospheric pressure. The core material was a mixture of 67.5 g of MMA-d8 that had been processed to have a water content of at most 100 ppm, a polymerization initiator, V-65, a chain transfer agent, Compound (1-1), and a dopant, diphenyl sulfide (DPS). In this, DPS was a non-polymerizable compound. The amount of V-65, that of Compound (1-1) and that of DPS in the mixture were 0.04 mol %, 0.2 mol % and 7 wt. %, respectively, of MMA-d8 therein. With its lengthwise direction kept horizontal, the chamber was rotated at 2300 rpm, in which the mixture was subjected to thermal polymerization at 70° C. for 2 hours. After 2 hours, the conversion of the core material was 90%. Next, this was subjected to thermal treatment at 120° C. for 24 hours while rotated at 500 rpm, thereby giving a core having a conversion of at least 99%. Next, while still rotated, this was spontaneously cooled to give a preform.

Thus obtained in this Example, the preform had a hollow in the center of the circular cross section of the core thereof, and its refractive index profile coefficient was 2.7. POF obtained by stretching the preform had an outer diameter of 500 μm and a length of 500 m. Thus obtained, POF was analyzed for its transmission loss at a light source wavelength of 650 nm, which was 66 dB/km.

COMPARATIVE EXAMPLE 2

Fabrication Example 2 of Plastic Optical Fiber, Using n-dodecanethiol as chain Transfer Agent A coated fiber was fabricated in the same manner as that of Example 2, for which, however, the same weight of n-dodecanethiol was used as the chain transfer agent in place of Compound (1-1). The coated fiber was analyzed for its transmission loss at a light source wavelength of 650 nm, which was 96 dB/km.

EXAMPLE 3

Fabrication Example 1 of Plastic Optical Fiber, Using Compound (2-9) as chain transfer agent A polymerization chamber having an inner surface of polyvinylidene fluorine and having an inner diameter of 18.5 mm and a length of 17 cm was prepared. A mixed solution was prepared by adding, to a mixture of 80 parts by weight of 2,2,2-trifluoroethyl methacrylate and 20 parts by weight of pentafluorophenyl methacrylate, dimethylazobisisobutyrate as a polymerization initiator in an amount of 0.1 mol % of all the monomers and Compound (2-9) as a chain transfer agent in an amount of 0.09 mol %. Thus prepared, the solution was purged with nitrogen for 5 minutes, and then filtered through a PTFE membrane filter (Whatman's Model 6784-1302). This was fed into the polymerization chamber, and sealed up with a Teflon® stopper. Next, the polymerization chamber was kept horizontal, and rotated at 2000 rpm, in which the monomers were thermally polymerized at 95° C. for 2 hours. This is a clad. Next, a mixed solution was prepared by adding, to a mixture of 76.2 parts by weight of 2,2,2-trifluoroethyl methacrylate and 23.8 parts by weight of pentafluorophenyl methacrylate, dimethylazobisisobutyrate as a polymerization initiator in an amount of 0.1 mol % of all the monomers and Compound (2-9) as a chain transfer agent in an amount of 0.09 mol %. Thus prepared, the solution was purged with nitrogen for 5 minutes, and then filtered through a PTFE membrane filter (Whatman's Model 6784-1302). This was injected into the hollow area of the clad. Then, the polymerization chamber was kept horizontal, and rotated at 2000 rpm, in which the monomers were thermally polymerized at 95° C. for 2 hours. This is the first layer of a core. Next, as in Table 1 below, other core layers up to the 10th layer were laminated on it, in the same manner as that for the formation of the first core layer. This was further heated at 95° C. for 6 hours, and a preform having an outer diameter of 18.5 mm and a hole diameter of 3 mm was finally obtained. The amount of the constitutive materials to be fed into the reactor was so controlled that the thickness of the clad could be 1.5 mm and the thickness of each core layer could be constant, 0.625 mm. Thus obtained, the preform was dried at 25° C. and under a reduced pressure of −0.1 MPa (as intended for full vacuum, corresponding to about 3 mmHg as calculated) for 100 hours, and then its hollow was connected to a degassing device. In that condition, this was thermally stretched in an electric furnace having an inner temperature of 200° C. under a reduced pressure of −4 KPa. Its hollow was lost, and 130 m of POF having an outer diameter of 470 μm was obtained. Thus obtained, the POF was analyzed for its refractive index profile with a two-flux transmission interference microscope (Mizojiri Optics' Model TD-20). Thus obtained, the refractive index profile data were processed for g-power approximation, and the refractive index profile coefficient, g, was 2. The transmission loss through the POF at a light source wavelength of 650 nm was measured, and it was 94 dB/km.

TABLE 1

| | Trifluoroethyl Methacrylate (wt. pts.) | Pentafluorophenyl Methacrylate (wt. pts.) |
|---|---|---|
| Clad | 80.00 | 20.00 |
| 1st Core Layer | 76.20 | 23.80 |
| 2nd Core Layer | 72.80 | 27.20 |
| 3rd Core Layer | 69.80 | 30.20 |
| 4th Core Layer | 67.20 | 32.80 |
| 5th Core Layer | 65.00 | 35.00 |
| 6th Core Layer | 63.20 | 36.80 |
| 7th Core Layer | 61.80 | 38.20 |
| 8th Core Layer | 60.80 | 39.20 |
| 9th Core Layer | 60.20 | 39.80 |
| 10th Core Layer | 60.00 | 40.00 |

COMPARATIVE EXAMPLE 3

Fabrication Example 3 of Plastic Optical Fiber, Using n-dodecanethiol as Chain Transfer Agent A coated fiber was fabricated in the same manner as that of Example 3, for which, however, the same weight of n-dodecanethiol was used as the chain transfer agent in place of Compound (2-9). The coated fiber was analyzed for its transmission loss at a light source wavelength of 650 nm, which was 120 dB/km.

EXAMPLE 4

Fabrication Example 2 of Plastic Optical Fiber, Using Compound (2-9) as Chain Transfer Agent POF was fabricated in the same manner as that of Example 3, for which, however, 2,2,2-trifluoroethyl methacrylate-d7 (all hydrogen atoms of trifluoroethyl methacrylate were deuterium atoms $^2H$) and pentafluorophenyl methacrylate-d5 (all hydrogen atoms of pentafluorophenyl methacrylate were deuterium atoms $^2H$) were used as monomers. Thus obtained, the POF was analyzed for its refractive index profile with a two-flux transmission interference microscope (Mizojiri Optics' Model TD-20). The refractive index profile data were processed for g-power approximation, and the refractive index profile coefficient, g, was 2. The transmission loss through the POF at a light source wavelength of 650 nm was measured, and it was 70 dB/km.

COMPARATIVE EXAMPLE 4

Fabrication Example 4 of Plastic Optical Fiber, Using n-dodecanethiol as Chain Transfer Agent A coated fiber was fabricated in the same manner as that of Example 4, for which, however, the same weight of n-dodecanethiol was used as the chain transfer agent in place of Compound (2-9). The coated fiber was analyzed for its transmission loss at a light source wavelength of 650 nm, which was 100 dB/km.

INDUSTRIAL APPLICABILITY

The invention provides an optical device having a reduced transmission loss, and provides a polymerizable composition capable of forming such an optical device.

The invention claimed is:

1. A compound of the following formula (1):

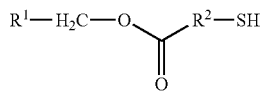

Formula (1)

wherein $R^1$ represents an alkyl group having from 1 to 3 carbon atoms and having at least one fluorine atom; and $R^2$ represents an alkylene group having 1 or 2 carbon atoms.

2. The compound as claimed in claim 1, wherein $R^1$ is a 2,2,2-trifluoroethyl group, a 2,2,3,3-tetrafluoropropyl group or a 2,2,3,3,3-pentafluoropropyl group.

3. The compound as claimed in claim 1, which has any of the following structures:

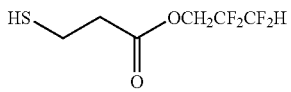
1-1

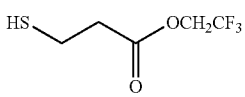
1-2

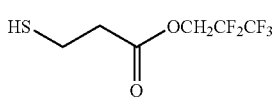
1-3

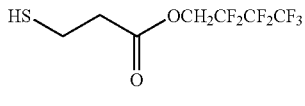
1-4

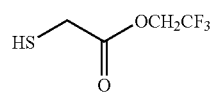
1-5

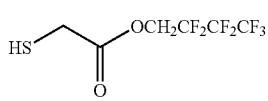
1-6

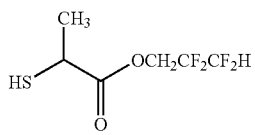
1-7

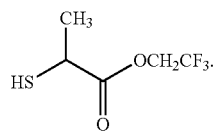
1-8

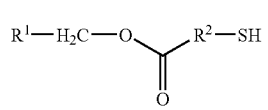
1-9

4. A polymerizable composition comprising a polymerizable monomer and a compound of the following formula (1):

Formula (1)

wherein $R^1$ represents an alkyl group having from 1 to 3 carbon atoms and having at least one fluorine atom; and $R^2$ represents an alkylene group having 1 or 2 carbon atoms.

5. The polymerizable composition as claimed in claim 4, wherein the polymerizable monomer is an acrylate and/or a methacrylate.

6. The polymerizable composition as claimed in claim 4, wherein a part or all of the hydrogen atoms which the polymerizable monomer has are deuterium atoms.

7. An optical device comprising a compound produced by polymerizing the polymerizable composition of claim 4 and having a refractive index profile region where the refractive index of the compound varies.

8. The optical device as claimed in claim 7, which is for optical communication using a light source at 900 nm or shorter.

9. The optical device as claimed in claim 7, which is for optical communication using a light source at 700 nm or shorter.

10. A method for producing an optical device having a core and a clad, which comprises polymerizing the polymerizable composition of claim 4 to form a core or a clad.

11. A method for producing a refractive index profile optical device, which comprises polymerizing the polymerizable composition of claim 4 in a cylindrical chamber to thereby form a core having a gradually increasing refractive index profile.

12. A refractive index profile optical device produced according to the production method of claim 11.

13. A method for producing a refractive index profile optical device, which comprises injecting a polymerizable composition for a clad into a cylindrical chamber rotating around the center axis thereof held horizontally and polymerizing it therein to form the clad, and then polymerizing a polymerizable composition for a core to form the core that has a refractive index profile gradually varying from the interface between it and the clad to the center thereof, and in which at least one of the polymerizable composition for the clad and the polymerizable composition for the core is the polymerizable composition of claim 4.

14. A refractive index profile optical device produced according to the production method of claim 13.

15. A method for producing a refractive index profile optical device, which comprises injecting the polymerizable composition of claim 4 into a cylindrical chamber rotating around the center axis thereof held horizontally and polymerizing it therein to form a clad, and then polymerizing the polymerizable composition of claim 4 to form a core that has a refractive index profile gradually varying from the interface between it and the clad to the center thereof.

16. A refractive index profile optical device produced according to the production method of claim 15.

17. An optical device comprising a compound of the following formula (1):

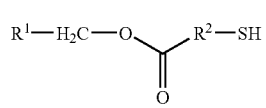

Formula (1)

wherein $R^1$ represents an alkyl group having from 1 to 3 carbon atoms and having at least one fluorine atom; and $R^2$ represents an alkylene group having 1 or 2 carbon atoms.

* * * * *